US00PP32831P3

(12) United States Plant Patent
van Heesbeen

(10) Patent No.: US PP32,831 P3
(45) Date of Patent: Feb. 23, 2021

(54) ***EUONYMUS* PLANT NAMED 'HEESGO1801'**

(50) Latin Name: *Euonymus japonicus*
Varietal Denomination: HEESGO1801

(71) Applicant: Van Heesbeen Cultures B.V., Rijsbergen (NL)

(72) Inventor: Ad van Heesbeen, Rijsbergen (NL)

(73) Assignee: Van Heesbeen Cultures B.V., Rijsbergen (NL)

( * ) Notice: Subject to any disclaimer, the term of this patent is extended or adjusted under 35 U.S.C. 154(b) by 0 days.

(21) Appl. No.: 16/501,669

(22) Filed: May 20, 2019

(65) Prior Publication Data

US 2019/0357398 P1 Nov. 21, 2019

(30) Foreign Application Priority Data

May 18, 2018 (QZ) ..... PBR 2018/1337

(51) Int. Cl.
*A01H 5/12* (2018.01)
*A01H 6/00* (2018.01)

(52) U.S. Cl.
USPC ..... Plt./246
CPC ..... *A01H 6/00* (2018.05); *A01H 5/12* (2013.01)

(58) Field of Classification Search
USPC ..... Plt./246
CPC ..... A01H 6/00
See application file for complete search history.

*Primary Examiner* — Anne Marie Grunberg
(74) *Attorney, Agent, or Firm* — Samuel R. McCoy, Jr.

(57) ABSTRACT

A new and distinct *Euonymus* plant named 'HEESGO1801' which is characterized by the combination of a large plant size, globular habit, yellow to green-yellow foliage, and the stability of these characteristics from generation to generation.

2 Drawing Sheets

Latin name of the genus and species: The Latin name of the genus and species of the novel variety disclosed herein is *Euonymus japonicus.*

Variety denomination: The inventive cultivar of *Euonymus* disclosed herein has been given the variety denomination 'HEESGO1801'.

CROSS REFERENCE TO RELATED APPLICATIONS

This application claims priority to the Community Plant Variety Rights application number 2018/1337, filed May 18, 2018, which is herein incorporated by reference.

BACKGROUND OF THE INVENTION

Parentage: 'HEESGO1801' originated as a naturally-occurring, whole plant mutation of an unnamed *Euonymus japonicus* plant (not patented). In June of 2016 the inventor discovered the mutation at a commercial greenhouse in Rijsbergen, the Netherlands, growing amongst a cultivated population of unnamed *Euonymus japonicus* plants. The mutation was noted for its unique foliage characteristics and was subsequently isolated for further evaluation in order to confirm the distinctness and stability of the characteristics first observed. Upon confirmation of distinctness and stability, the new *Euonymus* plant was selected for commercialization and given the name 'HEESGO1801'.

Asexual Reproduction: Asexual reproduction of 'HEESGO1801', by way of softwood stem cuttings, was first performed in June of 2016 in Rijsbergen, the Netherlands. Through five subsequent generations, the unique features of this cultivar have proven to be stable and true to type.

SUMMARY OF THE INVENTION

The cultivar 'HEESGO1801' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HEESGO1801'. These characteristics in combination distinguish 'HEESGO1801' as a new and distinct *Euonymus japonicus* cultivar:

1. *Euonymus* 'HEESGO1801' exhibits a relatively large plant size; and
2. *Euonymus* 'HEESGO1801' exhibits a globular plant shape; and
3. *Euonymus* 'HEESGO1801' exhibits light green-yellow stems; and
4. *Euonymus* 'HEESGO1801' exhibits foliage ranging in color from yellow to green-yellow.

BOTANICAL DESCRIPTION OF THE PLANT

Figure 1:
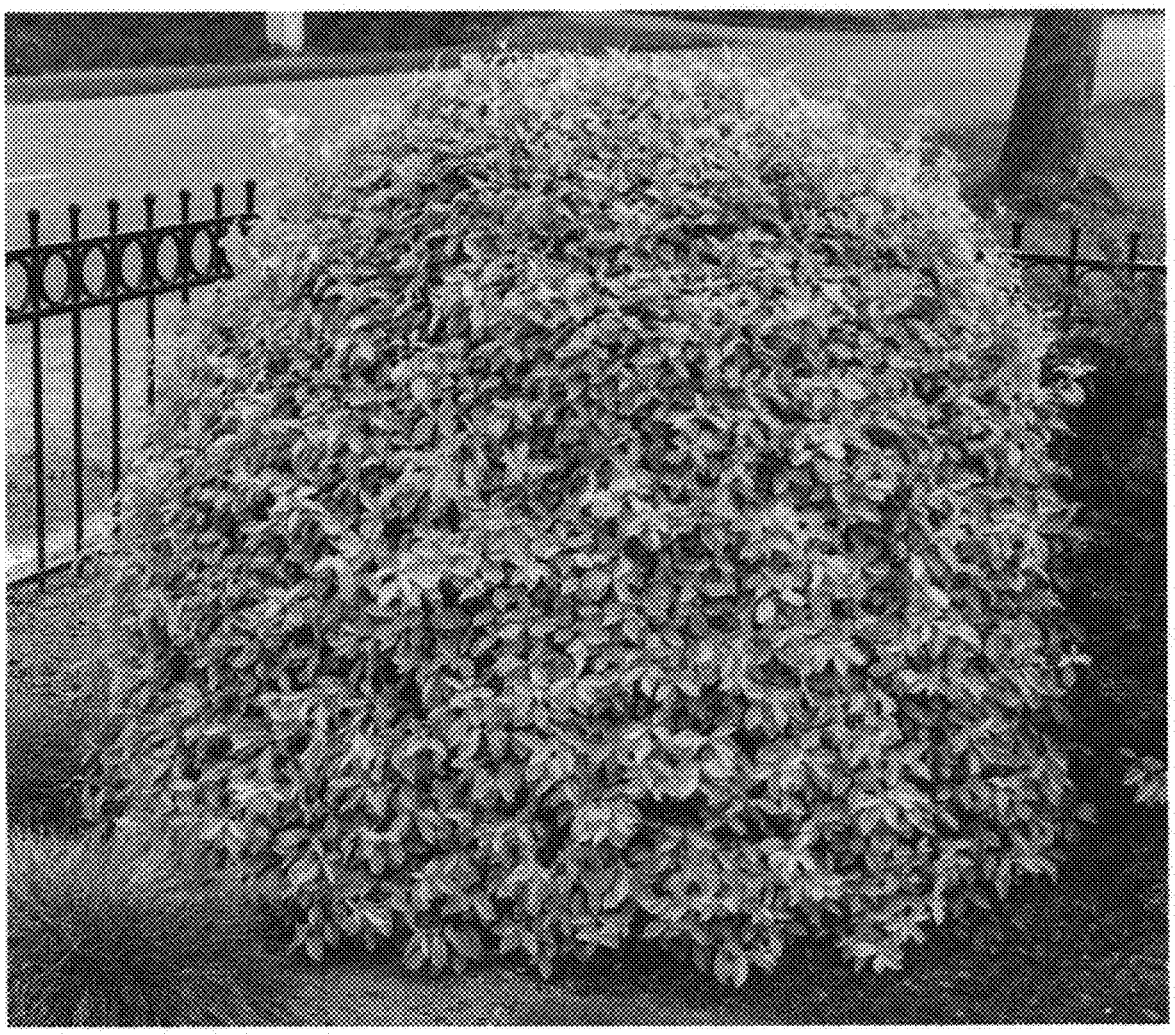
FIG. 1 illustrates, as nearly true as it is reasonably possible to make the same in color photographs of this type, an exemplary mature plant of 'HEESGO1801' grown outdoors in Rijsbergen, the Netherlands.
Figure 2:
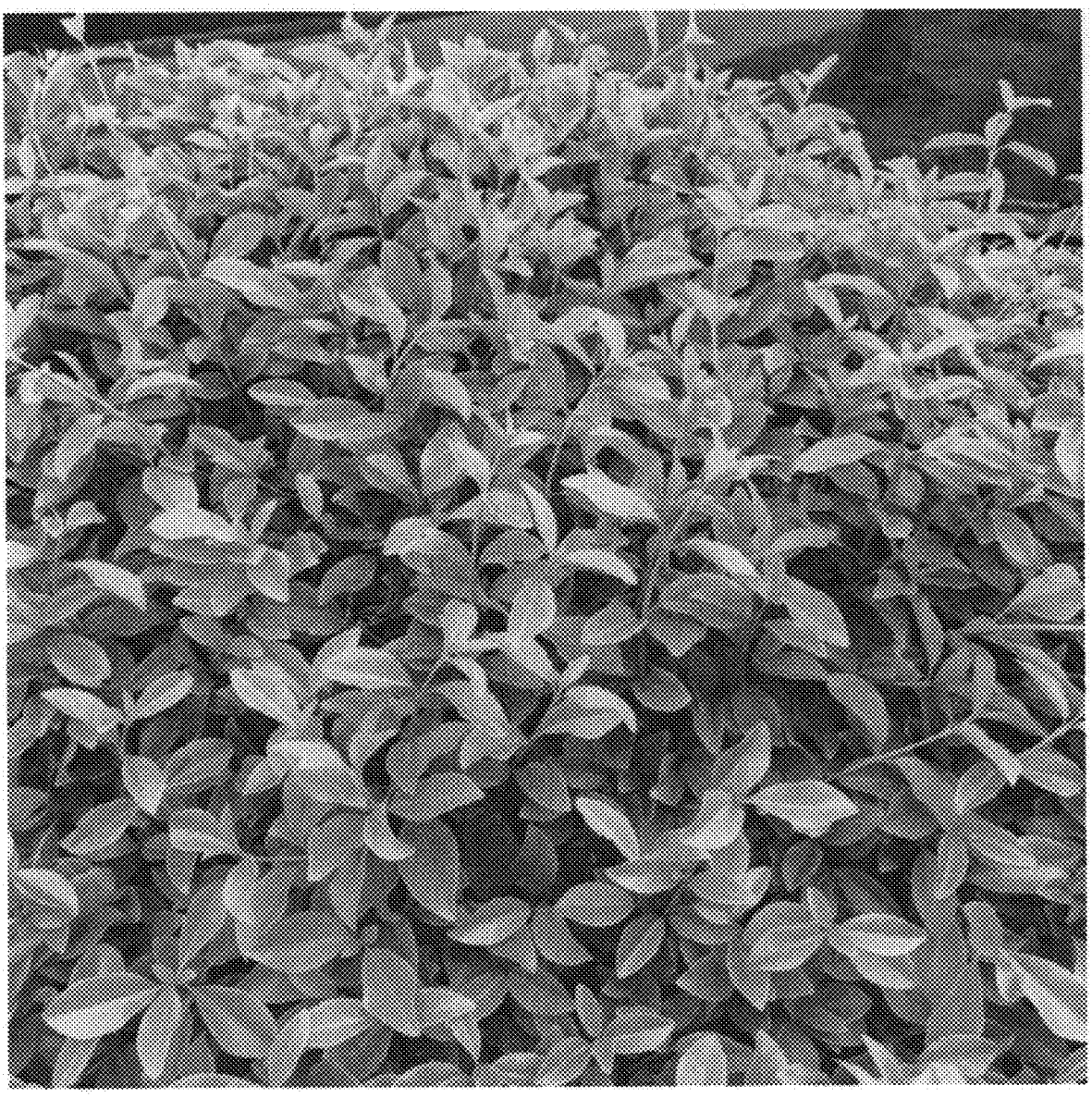
FIG. 2 illustrates, as nearly true as it is reasonably possible to make the same in color photographs of this type, the typical foliage of 'HEESGO1801'.

The following observations and measurements, made in August of 2019, describe averages from a sample set of six specimens of two year old 'HEESGO1801' plants grown in 23 cm nursery containers in Rijsbergen, the Netherlands. During the growing season, plants were produced outdoors with full sun exposure and maintained using overhead irrigation at regular intervals, and were fertilized as required using a slow release fertilizer. Plants were overwintered in unheated greenhouses. No chemical pest control measures were utilized during production.

Those skilled in the art will appreciate that certain characteristics will vary with older or, conversely, with younger plants. 'HEESGO1801' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 edition.

A botanical description of 'HEESGO1801' and comparisons with the parents and most similar variety of common knowledge are provided below.

General plant description:

*Growth habit*.—Perennial; broad spreading to upright.

*Plant form*.—Globular.

*Average height from base to top of foliage*.—28.7 cm.

*Average width*.—Average of 39.2 cm.

*Growth rate*.—Moderately fast growing.

*Plant vigor*.—Moderately vigorous.

*Propagation details*.—Method — Asexual propagation is accomplished by softwood stem cuttings. Time to initiate roots — Approximately 30 days are required to initiate roots at approximately 20 to 25 degrees Celsius. Time to produce a marketable 23 cm potted plant — Approximately 24 months.

*Disease and pest resistance or susceptibility*.—Neither tolerance nor resistance to normal diseases and pests of *Euonymus japonicus* have been observed.

*Environmental tolerances*.—Adapt to USDA Zones 6 to 9 and temperatures as high as 40 degrees Celsius; moderate tolerance to rain; moderate to high tolerance to wind.

Root system:

*General*.—Moderately fibrous; freely branched and moderately dense rooting.

*Distribution in the soil profile*.—Shallow to moderately deep.

*Diameter, mature roots*.—0.15 cm, on average.

*Texture*.—Smooth; glabrous.

*Color*.—Greyed-yellow, RHS 161C.

Stem:

*Branching habit*.—Main stem grows from the base, freely branching with lateral branches. Pinching isn't required but will improve branching.

*Number of main stems per plant*.—27.

*Number of lateral branches per plant*.—41.

*Aspect*.—Rounded.

*Attitude*.—Average angle is approximately 55 degrees from vertical.

*Strength*.—Strong.

*Length of lateral branches*.—16.7 cm.

*Diameter of lateral branches*.—Averaging 0.3 cm.

*Internode length on lateral branches*.—2.0 cm.

*Texture and luster*.—Smooth, glabrous, and matte.

*Color, juvenile*.—Yellow-green, nearest to RHS 144B AND 144C.

*Color, mature*.—Green, nearest to in between RHS 143B and 143C.

*Color at internodes*.—Green, nearest to in between RHS 143B and 143C.

*Color of oldest wood*.—Greyed-brown, nearest to a mixture of RHS 199A, 199B, and 199C.

Foliage:

*Arrangement*.—Opposite.

*Division*.—Simple.

*Attachment*.—Petiolate.

*Number of leaves per lateral branch*.—18.

*Lamina*.—Dimensions — 3.3 cm long and 2.0 cm wide, on average. Shape — Ovate. Attitude — Upward. Aspect — Slightly carinate and slightly reflexed. Apex — Obtuse. Base — Short attenuate to rounded. Margin — Crenate; slightly undulate. Texture and luster of adaxial surface — Glabrous, smooth, and very slightly glossy. Texture and luster of abaxial surface — Glabrous, smooth, and matte. Color — Juvenile foliage, adaxial surface — Yellow-green, nearest to RHS 144A. Juvenile foliage, abaxial surface — Yellow-green, nearest to a mixture of RHS 145A and 145B. Mature foliage, adaxial surface — Nearest to in between green and yellow-green, RHS NN137A and 147A, with approximately half of the foliar surface blotched and mottled with a mixture of yellow-green and yellow, nearest to RHS 145A, 151B, 4B, 6D, and 8C; occasionally the entire foliar surface is colored yellow, nearest to a mixture of RHS 6D and 8C. Mature foliage, abaxial surface — Green, nearest to RHS 139B, with approximately half of the foliar surface blotched and mottled with a mixture of yellow-green and yellow, nearest to RHS 144A, 144B, 144C, 4C, 8C, 8B, and 8C; occasionally the entire foliar surface is colored yellow, nearest to a mixture of RHS 8C and 8D. Venation — Pattern — Pinnate. Color, adaxial surface — Yellow-green, nearest to RHS 144B. In variegated leaves, the veins are colored nearest to a mixture of yellow-green and yellow; RHS 150B, 150C, and 8C. Color, abaxial surface — Yellow-green, nearest to RHS 144B. In variegated leaves, the veins are colored nearest to a mixture of yellow-green and yellow; RHS 150B, 150C, and 8C.

*Petiole*.—Length — 0.4 cm. Width — 0.1 cm. Texture and luster — Glabrous, smooth, and very slightly glossy. Strength — Strong. Color, adaxial surface — Yellow-green, nearest to a mixture of RHS 144C and 145A. In variegated leaves, petioles are colored yellow-green; nearest to a mixture of RHS 145C and 150C. Color, abaxial surface — Yellow-green, nearest to RHS 144B. In variegated leaves, petioles are colored yellow-green; nearest to a mixture of RHS 145B and 150C.

Inflorescence: To date, no flowering has been observed.

Flower buds: To date, no flowering has been observed.

Flower: To date, no flowering has been observed.

Reproductive organs: To date, no flowering has been observed.

Seed and fruit: To date, no flowering has been observed.

COMPARISONS WITH THE PARENT

Plants of the new cultivar 'HEESGO1801' differ from its parent, an unnamed *Euonymus japonicus* plant (not patented), by the characteristics described in Table 1.

TABLE 1

| Characteristic | 'HEESGO1801' | The parent. |
|---|---|---|
| Foliage size. | Smaller than the parent. | Larger than 'HEESGO1801'. |
| Foliage margin. | Crenate. | Finely denticulate. |
| General coloration of mature foliage. | A combination of green, yellow-green, and yellow with a high expression of yellow coloration. | Medium green. |

COMPARISONS WITH THE MOST SIMILAR VARIETY OF COMMON KNOWLEDGE

Plants of the new cultivar 'HEESGO1801' may be distinguished from the commercial variety *Euonymus japonicus* 'BR2012' (Community Plant Variety Rights application number 2016/0820; not patented in the United States) by the combination of characteristics described in Table 2.

TABLE 2

| Characteristic | 'HEESGO1801' | 'BR2012' |
|---|---|---|
| Growth habit. | Larger; less compact. | Smaller; more compact. |
| Mature foliage; distribution of yellow-colored foliage. | Entire plant. | Towards the apex. |

That which is claimed is:

1. A new and distinct cultivar of *Euonymus* plant named 'HEESGO1801', substantially as described and illustrated herein.

* * * * *